United States Patent
Li et al.

(10) Patent No.: US 8,867,812 B2
(45) Date of Patent: Oct. 21, 2014

(54) IMAGE SEGMENTATION OF ORGANS AND ANATOMICAL STRUCTURES

(75) Inventors: Senhu Li, Brentwood, TN (US); Brian Lennon, Nashville, TN (US); Jonathan Waite, Cary, NC (US); James Stefansic, Nashville, TN (US)

(73) Assignee: Pathfinder Therapeutics, Inc., Nashville, TN (US)

( * ) Notice: Subject to any disclaimer, the term of this patent is extended or adjusted under 35 U.S.C. 154(b) by 0 days.

(21) Appl. No.: 13/449,805

(22) Filed: Apr. 18, 2012

(65) Prior Publication Data

US 2013/0044930 A1 Feb. 21, 2013

Related U.S. Application Data

(60) Provisional application No. 61/476,744, filed on Apr. 18, 2011.

(51) Int. Cl.
| | |
|---|---|
| G06K 9/72 | (2006.01) |
| A61B 5/055 | (2006.01) |
| A61B 6/00 | (2006.01) |
| G06T 7/00 | (2006.01) |
| A61B 6/03 | (2006.01) |

(52) U.S. Cl.
CPC ....... *A61B 6/469* (2013.01); *G06T 2207/20036* (2013.01); *A61B 5/055* (2013.01); *A61B 6/5258* (2013.01); *G06T 2207/20108* (2013.01); *A61B 6/037* (2013.01); *A61B 6/5235* (2013.01); *G06T 7/0089* (2013.01); *G06T 7/0012* (2013.01); *A61B 6/032* (2013.01); *G06T 2207/10081* (2013.01); *A61B 6/501* (2013.01); *G06T 2207/20144* (2013.01); *G06T 2207/10088* (2013.01); *A61B 6/5211* (2013.01); *G06T 2207/10104* (2013.01)

USPC .......................................... 382/131; 382/128

(58) Field of Classification Search
USPC ......... 382/128, 130, 131, 132, 164, 171, 173, 382/194, 199, 203, 224, 254, 270, 274, 276, 382/286, 287, 291, 312; 378/4, 18, 20, 21, 378/23
See application file for complete search history.

(56) References Cited

U.S. PATENT DOCUMENTS

| | | | |
|---|---|---|---|
| 7,505,037 B2 | 3/2009 | Wang | |
| 7,620,226 B2 * | 11/2009 | Unal et al. | 382/128 |
| 7,689,021 B2 * | 3/2010 | Shekhar et al. | 382/131 |
| 2008/0193006 A1 | 8/2008 | Udupa et al. | |
| 2012/0082356 A1 * | 4/2012 | Zankowski | 382/131 |

OTHER PUBLICATIONS

International Search Report and Written Opinion for International Patent Application No. PCT/US2012/034030, mailed Nov. 30, 2012.

* cited by examiner

*Primary Examiner* — Gregory F Cunningham

(57) ABSTRACT

A system and method to conduct image segmentation by imaging target morphological shapes evolving from one 2-dimension (2-D) image slice to one or more nearby neighboring 2-D images taken from a 3-dimension (3-D) image. One area defined by a user as a target on an image slice can be found in a corresponding area on a nearby neighboring image slice by using a deformation field generated with deformable image registration procedure between these two image slices. It allows the user to distinguish target and background areas with the same or similar image intensities.

14 Claims, 5 Drawing Sheets

IMAGE SEGMENTATION OF ORGANS AND ANATOMICAL STRUCTURES

This application claims benefit of and priority to U.S. Provisional Application No. 61/476,744, filed Apr. 18, 2011, by Senhu Li, et al., and is entitled to that filing date for priority. The specification, figures and complete disclosure of U.S. Provisional Application No. 61/476,744 are incorporated herein by specific reference for all purposes.

FIELD OF INVENTION

This invention relates to a method and apparatus to distinguish the target and background areas with the same or similar image intensities for medical image segmentation purposes.

BACKGROUND OF THE INVENTION

Organ and anatomical structure segmentation is of importance in several medical applications, including the creation of surfaces used in image-guided surgical systems. A variety of prior art organ segmentation methods and systems are disclosed in Dawant, et al., U.S. Pat. No. 7,519,209, which is incorporated herein in its entirety by specific reference for all purposes.

One of the most difficult issues for segmentation on medical images is to define the adjunctions between two organs or anatomical structures that have the same or similar image intensities. The prior art often fails to distinguish targets from backgrounds in this situation.

Accordingly, what is needed is way to distinguish target and background areas with the same or similar image intensities for medical image segmentation purposes.

SUMMARY OF INVENTION

Image registration provides a method to define the corresponding points or elements between two images. These images may be images of organs or anatomical structures, and include, but are not limited to, human organs and anatomical structures. In various exemplary embodiments, the present invention comprises methods to conduct image segmentation by imaging target morphological shapes evolving from one 2-dimension (2-D) image slice to one or more nearby neighboring 2-D images taken from a 3-dimension (3-D) image. One area defined by a user as a target on an image slice can be found in a corresponding area on a nearby neighboring image slice by using a deformation field generated with deformable image registration procedure between these two image slices. It provides a solution to distinguish target and background areas with the same or similar image intensities, which is one of most difficult issues in the prior art, such as intensity-based region growing methods.

In one exemplary embodiment, the present invention utilizes the similarity of organ morphological structures on nearby neighboring image slices, and builds a deformation field between two nearby neighboring image slices by conducting image registration between these two image slices. Accordingly, when the target areas on one image slice are defined either by the user manually or from the previous segmentation step, the corresponding areas on the nearby neighboring image slice can be defined by applying the deformation field, even where the target and background areas are of the same or similar image intensities. In other words, the image registration between two slices helps distinguish the target and background areas even when they show same or similar image intensities. The user defines the target and background on one image slice, and the morphological structures on all other image slices can be deduced from it based on the deformation fields built with the image registration procedure.

While registration-based segmentation is known, the prior art does not conduct registration procedures to explore the similarity between neighboring cross section slices and use it to perform image segmentation. Other registration-based segmentation methods have developed to determine the transforms that map points on an object from one image to homologous points on the same object in a second image. In general, the two images contain the same contents and were taken at different times, so standard registration-based segmentation methods map the same object deformed over time. In contrast, the registration-based segmentation methods described herein map homologous points that represent the evolution of a shape from one cross section to its neighboring cross section, considering the human organs have smooth surfaces.

FIG. 1 shows a diagram of a method for organ segmentation using a deformation field in 3-D images in accordance with an exemplary embodiment of the present invention. In general, the top slice, referred to as the "seed image" slice, has a known target organ delineation before entering into the registration procedure. The bottom slice is referred to here as the "neighboring" slice, and is the slice on which the target organ delineation is derived.

FIG. 2 shows a chart of the steps of a method for organ segmentation using a deformation field in 3-D images. The first step is acquiring 3-D images of the organ of interest from the same or similar imaging modalities, such as (but not limited to), computed tomography (CT) images with or without contrast, magnetic resonance (MR) images of a same or similar pulse sequence, and positron emission tomography (PET) images. An image smoothing or filtering procedure may be applied if necessary to reduce image noise and facilitate the further image registration procedures.

Next, a 2-D seed image slice is selected, either manually or automatically. This is the first image slice that is delineated for the target organ, also manually or automatically. A 2-D deformable image registration procedure is then conducted between the seed image slice and its neighboring image slice. This generates a deformation field. A new delineation on the neighboring image slice is obtained by applying the deformation field onto the delineation from the seed image slice. Delineation refinement may or may not be needed after this step. With the new delineation and its corresponding 2-D image slice as the new seed image slice, the image registration procedure steps are repeated. The segmentation procedure stops when the area covered by 2-D delineation becomes particularly small or reaches a number smaller than a preset value or threshold.

DETAILED DESCRIPTION OF EXEMPLARY EMBODIMENTS

Image registration provides a method to define the corresponding points or elements between two images. In various exemplary embodiments, the present invention comprises methods to conduct image segmentation by imaging target morphological shapes evolving from one 2-dimension (2-D) image slice to one or more nearby neighboring 2-D images taken from a 3-dimension (3-D) image. One area defined by a user as a target on an image slice can be found in a corresponding area on a nearby neighboring image slice by using a deformation field generated with deformable image registration procedure between these two image slices. It provides a solution to distinguish target and background areas with the same or similar image intensities, which is one of most difficult issues in the prior art, such as intensity-based region growing methods.

Figure 1:
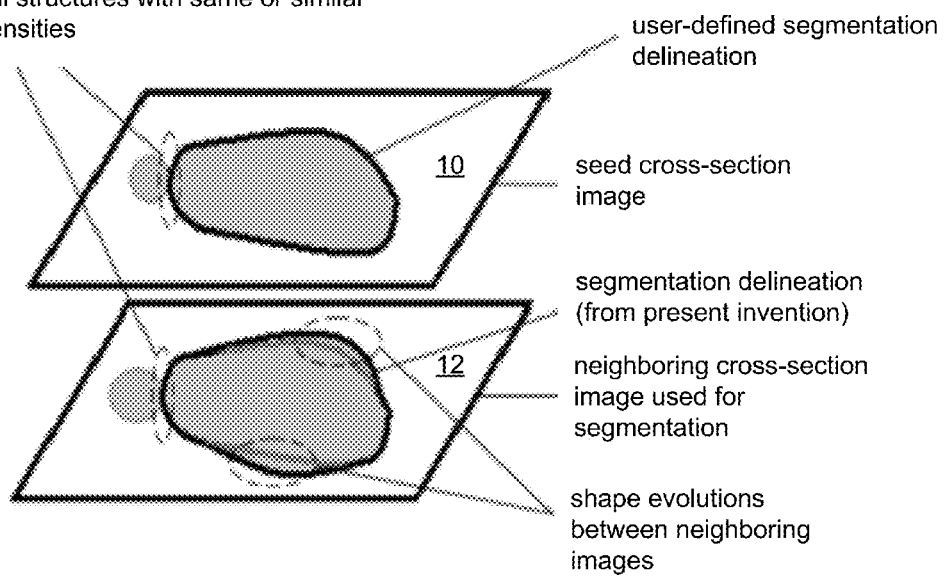
FIG. 1 shows a diagram of the segmentation method in accordance with an embodiment of the present invention.

In one exemplary embodiment, as shown in FIG. 1, the present invention utilizes the similarity of organ morphological structures on nearby neighboring image slices, and builds a deformation field between two nearby neighboring image slices by conducting image registration between these two image slices. Accordingly, when the target areas on one image slice are defined either by the user manually or from the previous segmentation step, the corresponding areas on the nearby neighboring image slice can be defined by applying the deformation field, even where the target and background areas are of the same or similar image intensities. In other words, the image registration between two slices helps distinguish the target and background areas even when they show same or similar image intensities. The user defines the target and background on one image slice, and the morphological structures on all other image slices can be deduced from it based on the deformation fields built with the image registration procedure.

While registration-based segmentation is known, the prior art does not conduct registration procedures to explore the similarity between neighboring cross section slices and use it to perform image segmentation. Other registration-based segmentation methods have developed to determine the transforms that map points on an object from one image to homologous points on the same object in a second image. In general, the two images contain the same contents and were taken at different times, so standard registration-based segmentation methods map the same object deformed over time. In contrast, the registration-based segmentation methods described herein map homologous points that represent the evolution of a shape from one cross section to its neighboring cross section, considering the human organs have smooth surfaces.

FIG. 1 shows two neighboring 2-D image slices, although it should be noted that the invention is not limited to the particular orientation of the 2-D image slices (e.g., axial, coronal, sagittal, or arbitrary). The top slice, referred to as the "seed image" slice 10, has a known target organ delineation before entering into the registration procedure. The bottom slice may be referred to as the "neighboring" slice 12, and is the slice on which the target organ delineation is derived.

Figure 2:
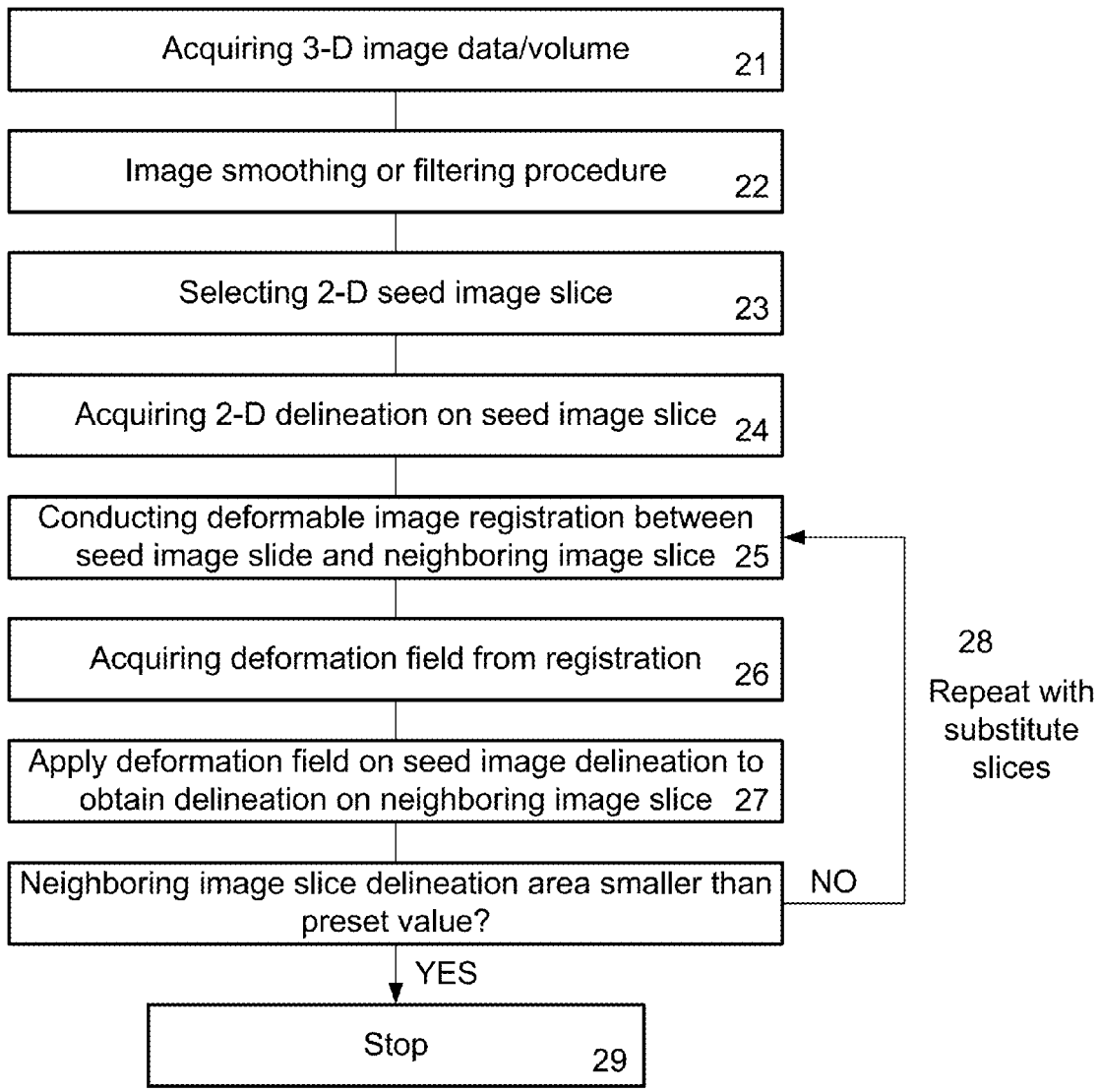
FIG. 2 shows a chart of the segmentation method in accordance with an embodiment of the present invention.

FIG. 2 shows a chart of the steps of a method for organ segmentation using a deformation field in 3-D images in accordance with an exemplary embodiment of the present invention. The first step 21 is acquiring 3-D image data or volume of the organ or structure of interest from the same or similar imaging modalities, such as (but not limited to), computed tomography (CT) images with or without contrast, magnetic resonance (MR) images of a same or similar pulse sequence, and positron emission tomography (PET) images. A image smoothing or filtering procedure 22 may be applied if necessary to reduce image noise and facilitate the further image registration procedures.

Next, a 2-D seed image slice is selected 23, either manually or automatically. This is the first image slice that is delineated 24 for the target organ, also manually or automatically. A 2-D deformable image registration procedure 25 is then conducted between the seed image slice and its neighboring image slice. This generates a deformation field 26. A new delineation on the neighboring image slice is obtained 27 by applying the deformation field onto the delineation from the seed image slice. Delineation refinement may or may not be needed after this step.

With the new delineation and its corresponding 2-D image slice as the new seed image slice, steps 25-27 are repeated 28. The segmentation procedure stops 29 when the area covered by 2-D delineation becomes particularly small or reaches a number smaller than a preset value or threshold.

Figure 3:
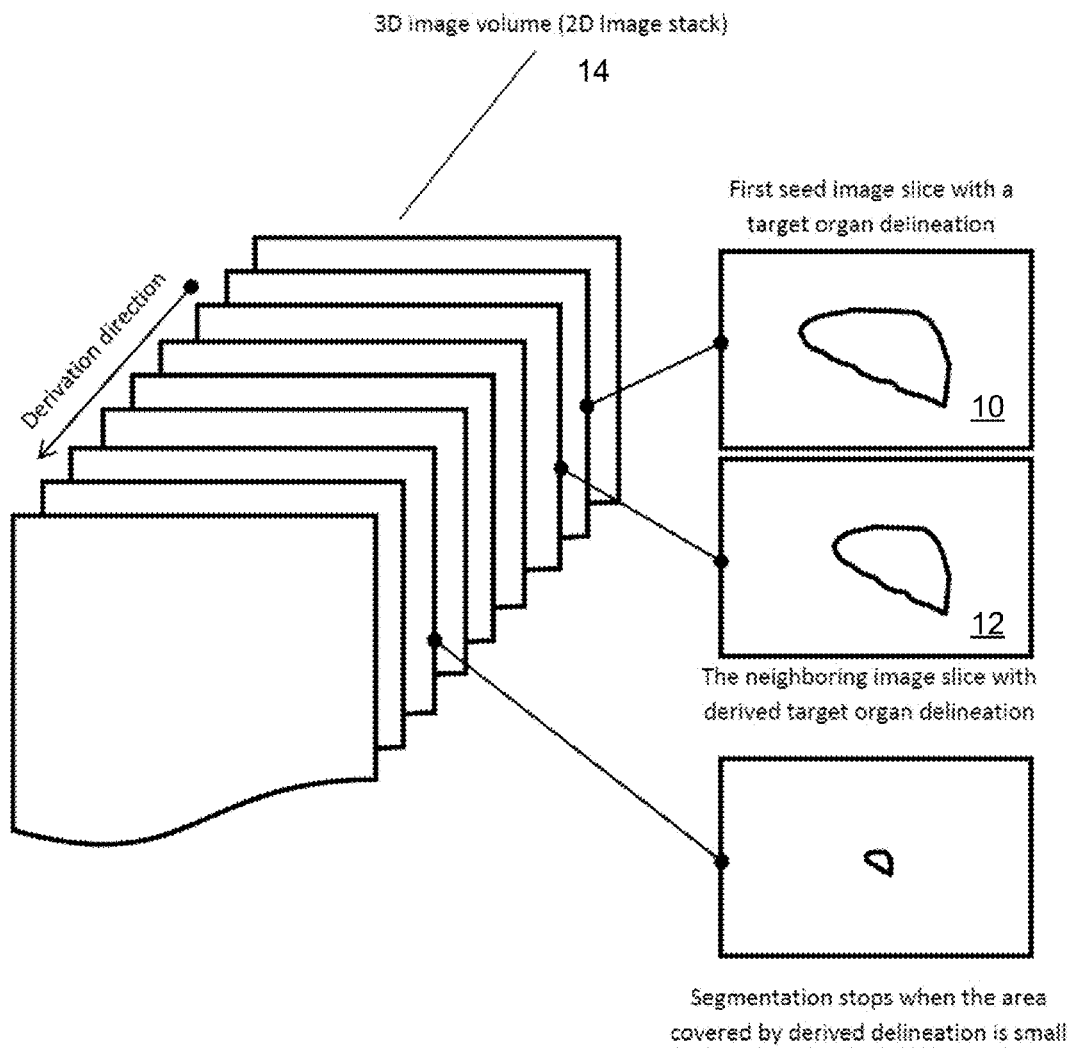
FIG. 3 shows a diagram of the method of FIG. 2.

FIG. 3 shows a diagram of an exemplary embodiment of a system of the present invention, as described above with respect to FIG. 2. Organ or anatomical structure segmentation is achieved using a deformation field generated with deformable image procedures between nearby neighboring 2-D image slices 10, 12 in the 3-D image volume 14. The process is carried out in conjunction with a computing device or computer with a microprocessor or processor coupled to a memory.

Figure 4:
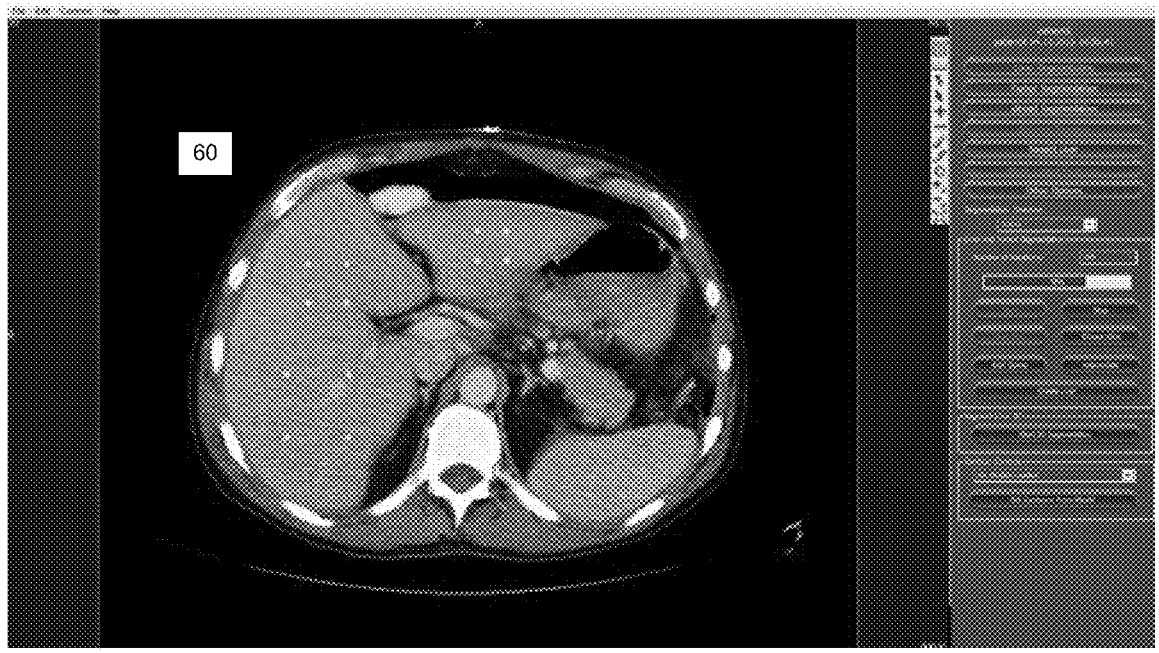
FIG. 4 shows an example of a user interface display showing a seed image slice.
Figure 5:
FIG. 5 shows an example of a user interface display showing the automated segmentation process.

FIG. 4 shows an exemplary user interface of the system of the present invention as shown on a computer display. The image shown is the initialization and result of the segmentation of the seed image slice 60. FIG. 5 shows the automated segmentation process being performed on neighboring slices sequentially 61, and the 3-D stacking 62 of the segmented slices as they are produced.

In order to provide a context for the various aspects of the invention, the following discussion provides a brief, general description of a suitable computing environment in which the various aspects of the present invention may be implemented. A computing system environment is one example of a suitable computing environment, but is not intended to suggest any limitation as to the scope of use or functionality of the invention. A computing environment may contain any one or combination of components discussed below, and may contain additional components, or some of the illustrated components may be absent. Various embodiments of the invention are operational with numerous general purpose or special purpose computing systems, environments or configurations. Examples of computing systems, environments, or configurations that may be suitable for use with various embodiments of the invention include, but are not limited to, personal computers, laptop computers, computer servers, computer notebooks, hand-held devices, microprocessor-based systems, multiprocessor systems, TV set-top boxes and devices, programmable consumer electronics, cell phones, personal digital assistants (PDAs), network PCs, minicomputers, mainframe computers, embedded systems, distributed computing environments, and the like.

Embodiments of the invention may be implemented in the form of computer-executable instructions, such as program code or program modules, being executed by a computer or computing device. Program code or modules may include programs, objections, components, data elements and structures, routines, subroutines, functions and the like. These are used to perform or implement particular tasks or functions. Embodiments of the invention also may be implemented in distributed computing environments. In such environments, tasks are performed by remote processing devices linked via a communications network or other data transmission medium, and data and program code or modules may be located in both local and remote computer storage media including memory storage devices.

In one embodiment, a computer system comprises multiple client devices in communication with at least one server device through or over a network. In various embodiments, the network may comprise the Internet, an intranet, Wide Area Network (WAN), or Local Area Network (LAN). It should be noted that many of the methods of the present invention are operable within a single computing device.

A client device may be any type of processor-based platform that is connected to a network and that interacts with one or more application programs. The client devices each comprise a computer-readable medium in the form of volatile and/or nonvolatile memory such as read only memory (ROM) and random access memory (RAM) in communication with a processor. The processor executes computer-executable program instructions stored in memory. Examples of such processors include, but are not limited to, microprocessors, ASICs, and the like.

Client devices may further comprise computer-readable media in communication with the processor, said media storing program code, modules and instructions that, when executed by the processor, cause the processor to execute the program and perform the steps described herein. Computer readable media can be any available media that can be accessed by computer or computing device and includes both volatile and nonvolatile media, and removable and non-removable media. Computer-readable media may further comprise computer storage media and communication media. Computer storage media comprises media for storage of information, such as computer readable instructions, data, data structures, or program code or modules. Examples of computer-readable media include, but are not limited to, any electronic, optical, magnetic, or other storage or transmission device, a floppy disk, hard disk drive, CD-ROM, DVD, magnetic disk, memory chip, ROM, RAM, EEPROM, flash memory or other memory technology, an ASIC, a configured processor, CDROM, DVD or other optical disk storage, magnetic cassettes, magnetic tape, magnetic disk storage or other magnetic storage devices, or any other medium from which a computer processor can read instructions or that can store desired information. Communication media comprises media that may transmit or carry instructions to a computer, including, but not limited to, a router, private or public network, wired network, direct wired connection, wireless network, other wireless media (such as acoustic, RF, infrared, or the like) or other transmission device or channel. This may include computer readable instructions, data structures, program modules or other data in a modulated data signal such as a carrier wave or other transport mechanism. Said transmission may be wired, wireless, or both. Combinations of any of the above should also be included within the scope of computer readable media. The instructions may comprise code from any computer-programming language, including, for example, C, C++, C#, Visual Basic, Java, and the like.

Components of a general purpose client or computing device may further include a system bus that connects various system components, including the memory and processor. A system bus may be any of several types of bus structures, including, but not limited to, a memory bus or memory controller, a peripheral bus, and a local bus using any of a variety of bus architectures. Such architectures include, but are not limited to, Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing and client devices also may include a basic input/output system (BIOS), which contains the basic routines that help to transfer information between elements within a computer, such as during start-up. BIOS typically is stored in ROM. In contrast, RAM typically contains data or program code or modules that are accessible to or presently being operated on by processor, such as, but not limited to, the operating system, application program, and data.

Client devices also may comprise a variety of other internal or external components, such as a monitor or display, a keyboard, a mouse, a trackball, a pointing device, touch pad, microphone, joystick, satellite dish, scanner, a disk drive, a CD-ROM or DVD drive, or other input or output devices. These and other devices are typically connected to the processor through a user input interface coupled to the system bus, but may be connected by other interface and bus structures, such as a parallel port, serial port, game port or a universal serial bus (USB). A monitor or other type of display device is typically connected to the system bus via a video interface. In addition to the monitor, client devices may also include other peripheral output devices such as speakers and printer, which may be connected through an output peripheral interface.

Client devices may operate on any operating system capable of supporting an application of the type disclosed herein. Client devices also may support a browser or browser-enabled application. Examples of client devices include, but are not limited to, personal computers, laptop computers, personal digital assistants, computer notebooks, hand-held devices, cellular phones, mobile phones, smart phones, pagers, digital tablets, Internet appliances, and other processor-based devices. Users may communicate with each other, and with other systems, networks, and devices, over the network through the respective client devices.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. A non-transitory processor readable medium storing code representing instructions to be executed by a processor configured to perform image segmentation, the code comprising code to cause the processor to:
receive 3-dimensional image data associated with a target and a background, the target including an anatomic structure, the background including tissue surrounding the anatomic structure;
select a 2-dimensional seed image slice from the 3-dimension image data;
define a first boundary of the target on the 2-dimensional seed image slice, the first boundary dividing the 2-dimensional seed image slice into a target portion associated with the target and a background portion associated with the background;
select a 2-dimensional neighboring image slice from the 3-dimensional image data;

generate a deformation field through deformable image registration conducted between the 2-dimensional seed image slice and the 2-dimensional neighboring image slice; and define a second boundary of the target on the 2-dimensional neighboring image slice by applying the deformation field to the first boundary of the target.

2. The non-transitory processor readable medium of claim 1, wherein the 2-dimensional seed image slice is a first 2-dimensional image slice, the 2-dimensional neighboring image slice is a second 2-dimensional image slice, and the deformation field is a first deformation field, the code further comprising code to cause the processor to:

select a third 2-dimensional image slice from the 3-dimensional image data;

generate a second deformation field through deformable image registration conducted between the second 2-dimensional image slice and the third 2-dimensional image slice; and define a third boundary of the target on the third 2-dimensional image slice by applying the second deformation field to the second boundary of the target.

3. The non-transitory processor readable medium of claim 1, the code further comprising code to cause the processor to:

define a plurality of boundaries of the target in addition to the first boundary and the second boundary, each boundary from the plurality of boundaries defined on a 2-dimensional image slice from a plurality of 2-dimensional image slices, the plurality of 2-dimensional image slices including the 2-dimensional seed image slice and the 2-dimensional neighboring image slice.

4. The non-transitory processor readable medium of claim 1, wherein the 3-dimensional image data is image data associated with at least one of computed tomography, magnetic resonance, or positron emission tomography.

5. The non-transitory processor readable medium of claim 1, wherein the anatomical structure is a human organ.

6. The non-transitory processor readable medium of claim 1, wherein the anatomical structure is a liver.

7. The non-transitory processor readable medium of claim 1, the code further comprising code to cause the processor to:

apply at least one of an image smoothing procedure or filtering procedure to the 3-dimensional image data.

8. The non-transitory processor readable medium of claim 1, the code further comprising code to cause the processor to:

send, to a display device, a signal to cause a 3-dimensional rendering of the target to be displayed on the display device.

9. The non-transitory processor readable medium of claim 1, the code further comprising code to cause the processor to:

send, to a display device, a signal to cause the 2-dimensional seed image slice to be displayed on the display device.

10. The non-transitory processor readable medium of claim 1, wherein the code to define the first boundary of the target includes code to define the first boundary of the target without receiving a user input that identifies the first boundary of the target.

11. The non-transitory processor readable medium of claim 1, wherein the code to define the first boundary of the target includes code to cause the processor to receive a user input that identifies the first boundary, the first boundary of the target defined in response to receiving the user input.

12. The non-transitory processor readable medium of claim 1, wherein a density gradient between the target and the background at a portion of the second boundary of the target is below a threshold density gradient such that the portion of the second boundary is not detectable based solely on the 2-dimensional neighboring image slice.

13. A non-transitory processor readable medium storing code representing instructions to be executed by a processor, the code comprising code to cause the processor to:

select a first 2-dimensional image from 3-dimensional image data associated with a target and a background, the target including an anatomic structure, the background including tissue surrounding the anatomic structure;

receive a signal associated with a user identifying the anatomical structure in the first 2-dimensional image;

define a first border of the anatomical structure in response to receiving the signal, the first border dividing the first 2-dimensional image into a target portion and a background portion;

select a second 2-dimensional image from the 3-dimensional image data; and define a second border of the anatomical structure on the second 2-dimensional image based on the first border of the anatomical structure using deformable image registration.

14. The non-transitory processor readable medium of claim 13, wherein a density gradient at a portion of the first border is approximately zero, such that the first border of the anatomical structure is not detectable without receiving the signal associated with the user identifying the anatomical structure.

* * * * *